(12) United States Patent
Kinoshita et al.

(10) Patent No.: US 8,734,418 B2
(45) Date of Patent: May 27, 2014

(54) PANT-TYPE WEARING ARTICLE AND METHOD FOR MAKING THE SAME

(75) Inventors: Akiyoshi Kinoshita, Kagawa (JP); Yasuhiko Kenmochi, Kagawa (JP)

(73) Assignee: Unicharm Corporation, Ehime (JP)

( * ) Notice: Subject to any disclaimer, the term of this patent is extended or adjusted under 35 U.S.C. 154(b) by 732 days.

(21) Appl. No.: 12/995,671

(22) PCT Filed: Apr. 20, 2009

(86) PCT No.: PCT/JP2009/057870
§ 371 (c)(1),
(2), (4) Date: Apr. 4, 2011

(87) PCT Pub. No.: WO2009/147907
PCT Pub. Date: Dec. 10, 2009

(65) Prior Publication Data
US 2011/0190721 A1    Aug. 4, 2011

(30) Foreign Application Priority Data

Jun. 3, 2008   (JP) .................................. 2008-146313

(51) Int. Cl.
*A61F 13/15*    (2006.01)
*B32B 37/00*    (2006.01)

(52) U.S. Cl.
USPC ............ 604/385.25; 604/385.24; 604/385.26; 604/385.27; 604/385.29; 604/385.3; 156/256; 156/257

(58) Field of Classification Search
USPC ............. 604/385.24, 385.25, 385.26, 385.27, 604/385.29, 385.3; 156/167, 256, 252, 267
See application file for complete search history.

(56) References Cited

U.S. PATENT DOCUMENTS

| 6,454,751 B1 * | 9/2002 | Olson ........................ 604/389 |
| 2002/0007172 A1 | 1/2002 | Takei et al. |
| 2004/0230171 A1 | 11/2004 | Ando et al. |
| 2005/0043698 A1 | 2/2005 | Otsubo et al. |
| 2005/0080394 A1 | 4/2005 | Otsubo et al. |
| 2005/0267431 A1 | 12/2005 | Sasaki et al. |
| 2008/0249493 A1 | 10/2008 | Kobayashi et al. |

FOREIGN PATENT DOCUMENTS

| EP | 1 795 163 A1 | 6/2007 |
| JP | 6-52818 | 7/1994 |
| JP | 2002-035029 | 2/2002 |
| JP | 2002-035030 | 2/2002 |

(Continued)

OTHER PUBLICATIONS

International Search Report from corresponding PCT application No. PCT/JP2009/057870 dated Jul. 21, 2009, 4 pgs.

(Continued)

*Primary Examiner* — Jacqueline F. Stephens
(74) *Attorney, Agent, or Firm* — Brinks Gilson & Lione

(57) ABSTRACT

A pant-type wearing article configured so that fasteners used to connect front and rear waist regions with each other can be engaged with and disengaged from each other in a repetitive manner. Of the front and rear waist regions, at least one waist region, for example, the front waist region is formed in its transversely opposite lateral zones with inelastic regions being neither elastically stretchable nor elastically contractible in a waistline direction. These inelastic regions are provided with first fastener members selected from the first fastener members and second fastener members. The front waist region is further formed inside the respective inelastic regions as viewed in the waistline direction with a plurality of film-like joints defined by integrated sheet members forming the lateral zones.

14 Claims, 6 Drawing Sheets

(56) References Cited

FOREIGN PATENT DOCUMENTS

| JP | 2002-253605 | 9/2002 |
| JP | 2005-095574 | 4/2005 |
| JP | 2005-261958 | 9/2005 |
| JP | 2006-087564 | 4/2006 |
| JP | 2006-087568 | 4/2006 |

OTHER PUBLICATIONS

European Search Report from corresponding European Application No. 09758174.8 dated Jan. 9, 2014 (7 pages).

* cited by examiner

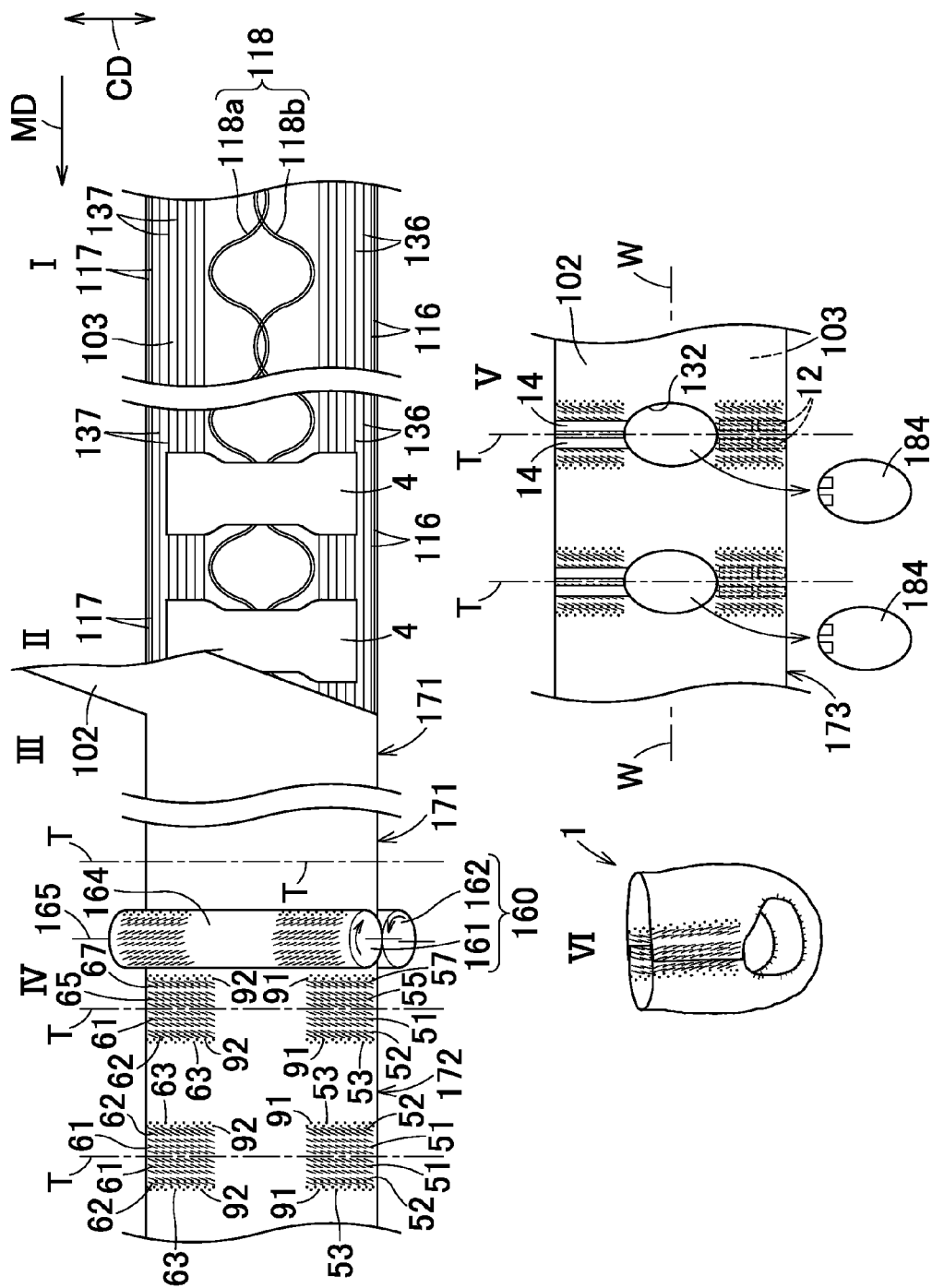

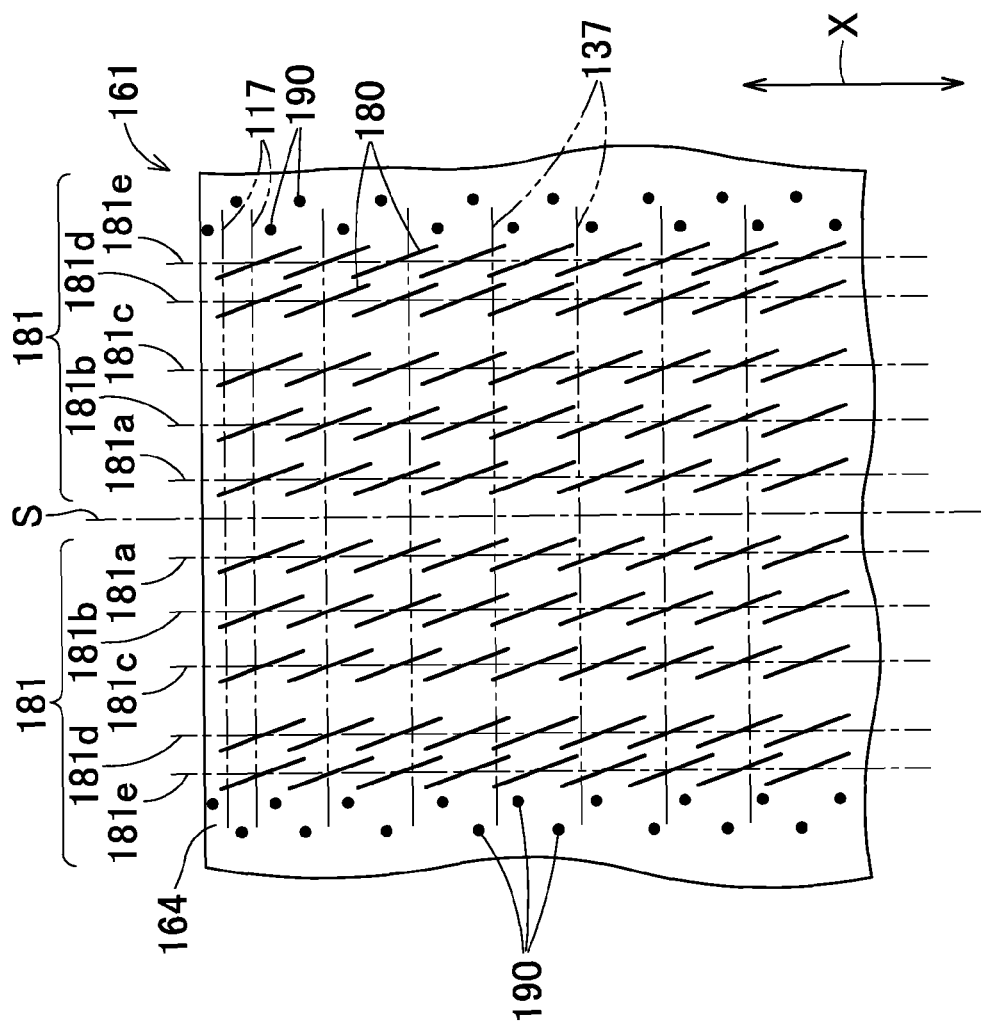

US 8,734,418 B2

PANT-TYPE WEARING ARTICLE AND METHOD FOR MAKING THE SAME

RELATED APPLICATION

This application is a 35 U.S.C. §371 national phase filing of International Patent Application No. PCT/JP2009/057870, filed Apr. 20, 2009, through which and to which priority is claimed under 35 U.S.C. §119 to Japanese Patent Application No. 2008-146313, filed Jun. 3, 2008.

TECHNICAL FIELD

The present invention relates to pant-type wearing articles suitable to be used as disposable diapers or disposable toilet-training pants and also to methods for making the same.

RELATED ART

Various designs have already been proposed for pant-type wearing articles having front and rear waist regions adapted to be connected with each other along respective pairs of transversely opposite lateral zones thereof via a fastener in a manner that these lateral zones may be unfastened and, if desired, refastened. For example, a disposable absorbent article disclosed in JP 2005-95574 A (PATENT DOCUMENT 1) is provided along the respective pairs of transversely opposite lateral zones of front and rear waist regions with fastener members each extending from a peripheral edge of a waist opening to respective peripheral edges of leg-openings. The fastener members provided along the lateral zones of the front waist region are engaged with the associated fastener members provided along the lateral zones of the rear waist region to achieve a desired function as the fastener. During a production process for this absorbent article, the respective lateral zones of the front and rear waist regions along which these fastener members are attached are pretreated to become inelastic. To obtain such inelastic lateral zones, respective elastic members extending under tension across the front and rear waist regions in initial several steps are left contract only along the lateral zones in the subsequent step using a known snap-back technique.
[PATENT DOCUMENT 1] JP 2005-95574 A

DISCLOSURE OF THE INVENTION

Problem to be Solved by the Invention

In the case of the absorbent article disclosed in PATENT DOCUMENT 1, repeated engagement and disengagement between the front and rear waist regions via the fasteners may sometimes lead to breaks of the sheet members occurring in the vicinity of boundaries between the fastener members and the sheet member to which these fastener members attached and eventually such breaks may propagate. In view of the problem as has been described just above, it is an object of the present invention to improve the wearing article of prior art so as to prevent the sheet member defining the lateral zones from being broken or torn and so as not to eventually propagate such break or tear even if engagement and disengagement between the front and rear waist members are repeated.

Measure to Solve the Problem

The object set forth above is achieved by an improvement in a pant-type wearing article according to the present invention on a first aspect thereof and by an improvement in a method for making the same according to the present invention on a second aspect thereof.

On the first aspect, the present invention relates to an improvement in a pant-type wearing article comprising a first waist region defined by one of front and rear waist regions, a second waist region defined by other of front and rear waist regions and a crotch region extending between these first and second waist regions wherein respective inner surfaces of second fastener members provided along transversely opposite lateral zones of the second waist region are detachably engaged with respective outer surfaces of first fastener members provided along transversely opposite lateral zones of the first waist region to obtain the pant-type wearing article having a waist-opening and a pair of leg-openings formed upon the engagement.

The improvement in the wearing article according to the present invention on the first aspect thereof is characterized as described below. At least one waist region of the first waist region and the second waist region includes a plurality of elastic members bonded thereto under tension so as to extend across the one waist region and, in the transversely opposite lateral zones of the one waist region, the elastic members are respectively cut at several points in a longitudinal direction thereof to form inelastic regions being neither elastically stretched nor elastically contractible in the longitudinal direction. The first fastener members or the second fastener members both provided in the one waist region are provided in the inelastic regions. Transversely opposite lateral zones of the one waist region are formed inside the inelastic regions as viewed in a waistline direction with a plurality of film-like joints comprising sheet members put flat together to define the transversely opposite lateral zones and integrated or comprising the sheet members and the elastic members integrated and the joints define joint areas extending in a vertical direction of the wearing article from the waist-opening to the leg-openings.

According to one preferred embodiment of the present invention on this first aspect, the elastic members are respectively cut in the one waist region also in regions spaced inward from the inelastic regions as viewed in the waistline direction so as to form the joints in regions further spaced inward from the regions formed spaced inward from the inelastic regions.

According to another preferred embodiment of the present invention on this first aspect, at least one of the sheet members put flat together comprises thermoplastic synthetic fiber and, at a plurality of the joints at which the elastic members are cut, components of the thermoplastic synthetic fiber are melt-solidified together.

According to still another preferred embodiment of the present invention on this first aspect, the sheet members are melt-solidified together at the joints.

On the second aspect, the present invention relates to an improvement in a method for making a pant-type wearing article comprising a first waist region defined by one of front and rear waist regions, a second waist region defined by the other of the front and rear waist regions and a crotch region extending between the first and second waist regions wherein respective inner surfaces of the second fastener members provided along transversely opposite lateral zones of the second waist region are detachably engaged with respective outer surfaces of first fastener members provided along transversely opposite lateral zones of the first waist region to obtain the pant-type wearing article having a waist-opening and a pair of leg-openings formed upon the engagement.

The improvement in such method according to the present invention on the second aspect thereof is characterized as described below. At least one of the first waist region and the second waist region includes a plurality of elastic members bonded thereto under tension so as to extend across the one waist region and, in the transversely opposite lateral zones of the one waist region, the elastic members are respectively cut at several points in a longitudinal direction thereof to form inelastic regions being neither elastically stretched nor elastically contractible in the longitudinal direction. The first fastener members or the second fastener members both provided in the one waist region are provided in the inelastic regions. Transversely opposite lateral zones of the one waist region are formed inside the inelastic regions as viewed in a waistline direction with a plurality of film-like joints comprising sheet members put flat together to define the transversely opposite lateral zones and integrated or comprising the sheet members and the elastic members integrated and the joints define joint areas extending in a vertical direction of the wearing article from the waist-opening to the leg-openings. The inelastic regions and the joint areas are formed by following at least the steps of:

a. subjecting a composite web to a cutter at regular intervals in the machine direction, wherein the composite web comprises first and second webs put flat and bonded together by adhesive and continuously fed in a machine direction and a plurality of continuous elastic members sandwiched between the first and second webs so as to extend in the machine direction and bonded under tension to at least one of the first and second webs, the thereby cutting the continuous elastic members at several points within predetermined ranges of the composite web to obtain the inelastic regions within the predetermined ranges; and b. using a plurality of pins to pressurizing, with or without heating, the composite web comprising the first and second webs put flat and bonded together by adhesive and continuously fed in the machine direction and a plurality of the continuous elastic members sandwiched between the first and second webs so as to extend in the machine direction and bonded under tension to at least one of the first and second webs in a plurality of points lying inside the predetermined ranges of the composite web to be formed with the inelastic regions as viewed in the machine direction and thereby forming a plurality of joints at which the first web and the second web are integrated together in a film or at which the first web, the second web and the continuous elastic members are integrated together in a film so that these joints are distributed in a cross direction with respect to the machine direction and thereby the joint areas are obtained.

According to one preferred embodiment of the present invention on the second aspect thereof, at least one of the first and second webs comprises thermoplastic synthetic fiber and the cutter and the pins constituting a single roll adapted to be rotated in the machine direction and to be heated so that components of the thermoplastic synthetic resin are melt-solidified together at a plurality of the points at which the continuous elastic members are cut and a plurality of the points at which the joints are formed.

Effect of the Invention

The pant-type wearing article and the method for making the same according to the present invention is characterized in that the inelastic regions in at least one of the first waist region and the second waist region to be provided with the first fastener members or the second fastener members are formed by cutting the respective elastic members at a plurality of points arranged in the longitudinal direction of these elastic members. Such unique design allows the sheet members put flat together in the transversely opposite lateral zones of the one waist region in which the inelastic regions are formed to be bonded together by adhesive before the elastic members are cut. Aside inward from these inelastic regions as viewed in the waistline direction, the lateral zones are provided with a plurality of the film-like joints formed by the sheet members put flat and integrated together or a plurality of the film-like joints formed by the sheet members and the elastic members put flat and integrated together so as to define the joint areas. With such unique design, even if the sheet members are broken or torn along the respective boundaries between the sheet members and the first fastener members and/or the second fastener members, the film-like joints defining the respective joint areas prevent such break or tear from propagating. The film-like joints of the sheet members and the elastic members prevent the elastic members from being immobilized together with the sheet members from contracting.

BRIEF DESCRIPTION OF THE DRAWINGS

FIG. 5 is a diagram schematically illustrating a production process for the diaper.

FIG. 6 is a partial view of the first roll.

Figure 1:
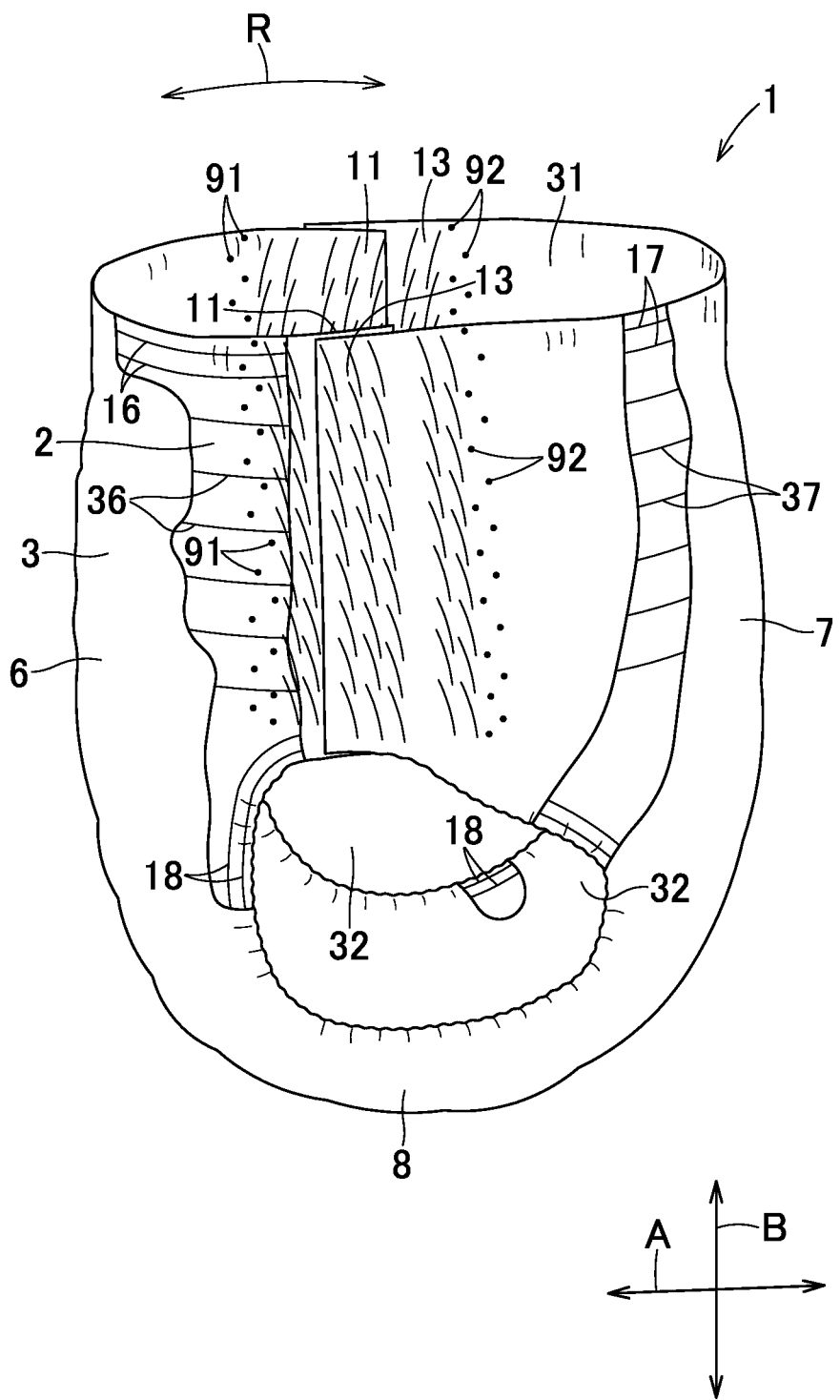
FIG. 1 is a side view showing a diaper as partially broken away.

IDENTIFICATION OF REFERENCE NUMERALS USED IN THE DRAWINGS 1 absorbent article (diaper)
6 front waist region
7 rear waist region
8 crotch region
11 lateral zone (front lateral zone)
12 first fastener member (front fastener member)
13 lateral zone (rear lateral zone)
14 second fastener member (rear fastener member)
16 elastic member
17 elastic member
18 elastic member
36 elastic member
37 elastic member
51 inelastic region
52 inelastic region
53 joint area
61 inelastic region
62 inelastic region
63 joint area
91 joint
92 joint
102 first web (web)
103 second web (web)
116 elastic member
117 elastic member
118 elastic member
136 elastic member
137 elastic member
160 cutter
180 blade segment
190 pin (projection)

A front-back direction
B vertical direction
MD machine direction

DETAILED DESCRIPTION OF THE PREFERRED EMBODIMENTS

The pant-type wearing article and the method for making the same will be described hereunder in more details with reference to the accompanying drawings.

Figure 2:
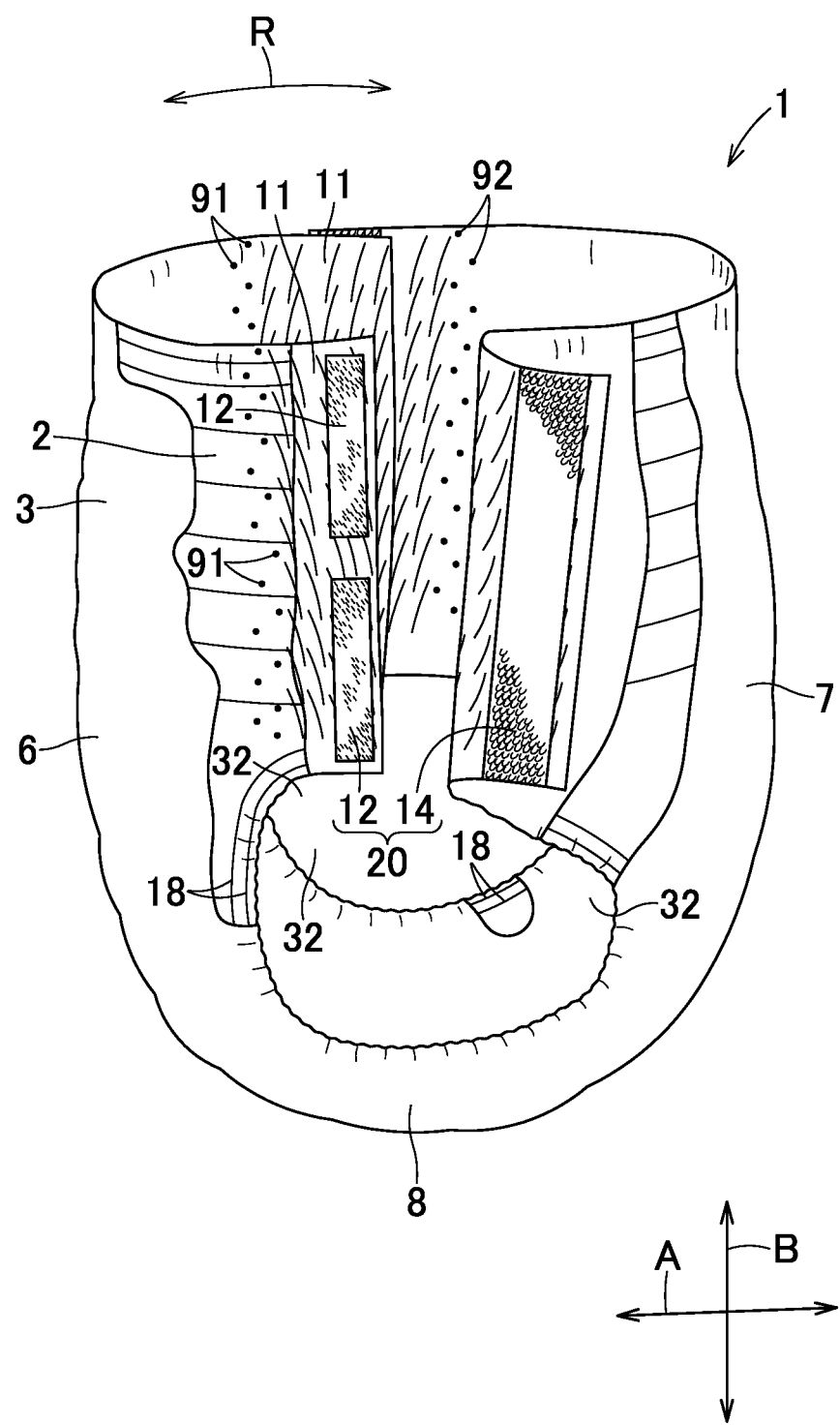
FIG. 2 is a view similar to FIG. 1, showing a diaper having one of lateral zones thereof opened.

FIG. 1 is a partially cutaway side view showing a diaper 1 as an example of a pant-type wearing article according to the present invention and FIG. 2 is a partially cutaway side view showing the diaper 1 having one of lateral zones thereof opened. A front-back direction, a vertical direction and a circumferential direction are indicated by double-headed arrows A, B and R, respectively. The diaper 1 has a front waist region 6, a rear waist region 7 and a crotch region 8 extending between these two waist regions 6, 7. These regions 6, 7 and 8 respectively comprise a liquid-pervious inner sheet 2, a liquid-impervious outer sheet 3 and a body fluid absorbent core 4 (See FIG. 3) sandwiched between these two sheets 2, 3. In the front waist region 6, front lateral zones 11 opposite in the waistline direction R and extending in the vertical direction B are provided on respective outer surfaces thereof with front fastener members 12 attached thereto (See FIG. 2). In the rear waist region 7, rear lateral zones 13 opposite in the waistline direction R and extending in the vertical direction B are provided with rear fastener members 14 attached thereto. The inner sheet 2 is formed, for example, of a nonwoven fabric made of thermoplastic synthetic fibers and the outer sheet 3 is formed, for example, of a thermoplastic synthetic resin film, a nonwoven fabric made of thermoplastic fibers or a composite sheet comprising these film and nonwoven fabric.

The front fastener members 12 are associated with the rear fastener members 14 to form fasteners 20 for connecting the front and rear waist regions 6, 7 in a manner that these waist regions are able to be unfastened and refastened, respectively, wherein the hook members constituting the mechanical fastener widely known in the trade name of Magic Tape are used here as the front fastener members 12 and the loop members constituting this mechanical fastener are used here as the rear fastener members 14. FIG. 1 shows the diaper 1 wherein a pair of front lateral zones 11 is connected with a pair of the associated rear lateral zones 13 via the fasteners 20 and FIG. 2 shows the diaper 1 wherein a pair of front lateral zones 11 is connected with a pair of the associated rear lateral zones 13 via the fasteners 20 on the remote side and a pair of front lateral zones 11 has been disengaged from the associated rear lateral zones 13 on the near side. Obviously, the pant-type disposable diaper according to the invention can be put on and taken off from the wearer in the same manner as the diaper of prior art. The diaper according to the invention is distinguished from the diaper of prior art in that it is easy for the inventive diaper to open one of the lateral zones and thereby to check whether urination and/or defecation has occurred or not even when the wearer is in upright posture. This advantage can be effectively utilized by the user particularly when the diaper is delivered to the user in the pant-shape.

Referring to FIG. 1, the front and rear waist regions 6, 7 are detachably connected to each other and thereupon a waist-opening 31 and a pair of leg-openings 32 are formed, in other words, the diaper 1 is shaped into a pant. The front fastener members 12 and the rear fastener members 14 respectively extend from the waist-opening 31 to the leg-openings 32. It should be noted that, in the illustrated embodiment, the front fastener members 12 are respectively divided into upper and lower portions.

Figure 3:
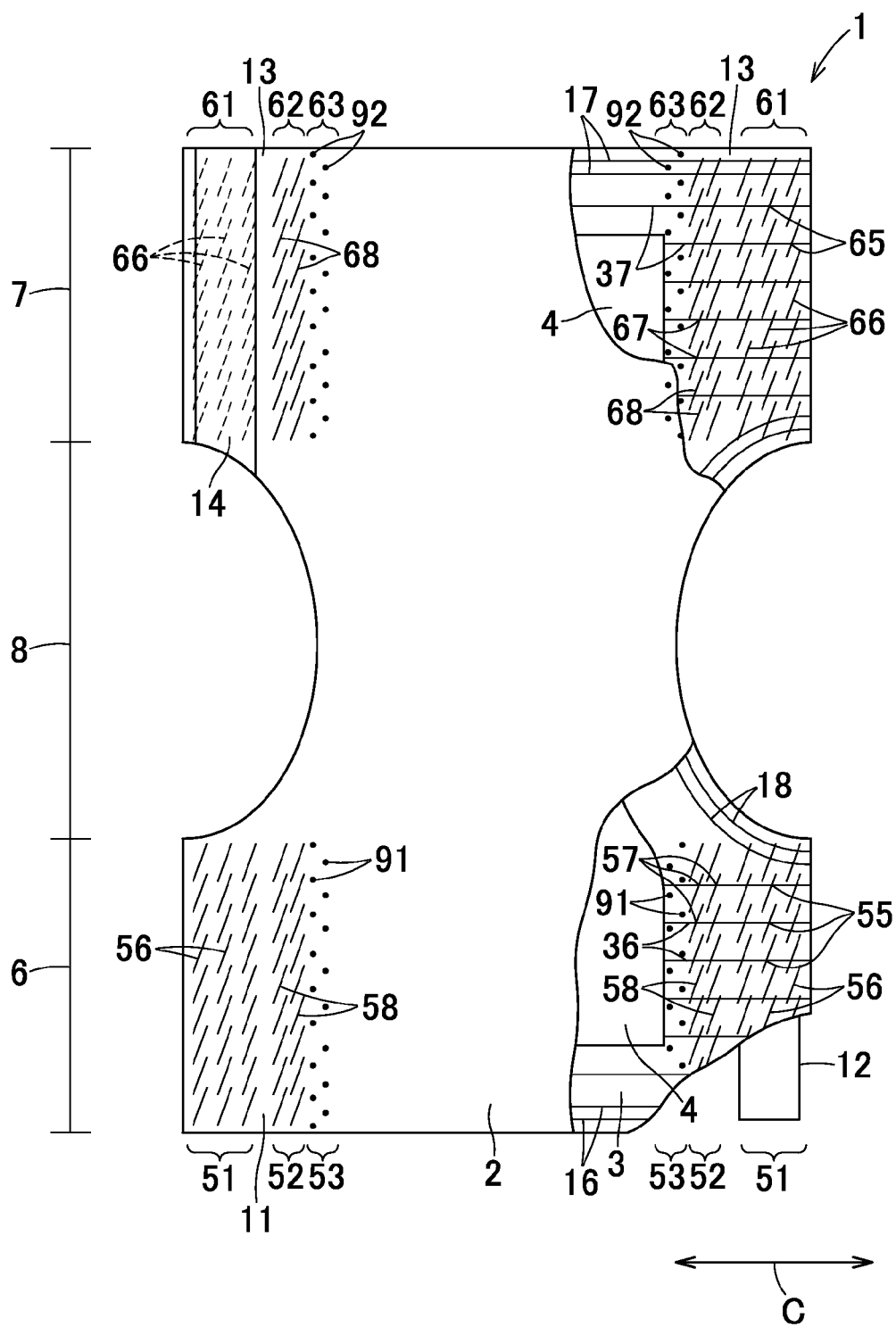
FIG. 3 is a partially cutaway plan view showing the diaper as a front waist region and a rear waist region thereof have been disconnected from each other and flatly developed.

FIG. 3 is a partially cutaway plan view of the diaper 1 with the front waist region 6 and the rear waist region 7 having been connected together via the fasteners 20 in the phase of FIG. 1 being disengaged from each other and flatly developed wherein a transverse direction of the front and rear waist regions 6, 7 is indicated by a double-headed arrow C. In the diaper 1 shown by FIG. 3, the core 4 illustrated herein as partially broken away has a concave shape curved inwardly. The inner and outer sheets 2, 3 sandwich the core 4 therebetween extend outward beyond a peripheral edge of the core 4 and bonded to each other in these portions extending outward by hot melt adhesive (not shown) coated intermittently and evenly on these portions. These portions of the inner and outer sheets 2, 3 extending outward include the front lateral zones 11 and the rear lateral zones 13. The inner and outer sheets 2, 3 are bonded also to upper and lower surfaces of the core 4 by hot melt adhesive (not shown).

Various elastic members are sandwiched between the inner and outer sheets 2, 3. Specifically, the front waist region 6 is provided with waist elastic members 16 extend under tension in the transverse direction C, the rear waist region 7 is provided with waist elastic members 17 extending under tension in the transverse direction C and the crotch region 8 is provided with leg elastic members 18 extending under tension so as to describe curves along respective peripheral edges of the leg-openings 32. In addition to these elastic members, front intermediate elastic members 36 are provided between the front waist-biasing elastic members 16 and the leg elastic members 18 so as to extend under tension in the transverse direction C and rear intermediate elastic members 37 provided between the rear waist-biasing elastic members 17 and the leg elastic members 18 so as to extend under tension in the transverse direction C. These elastic members 16, 17, 18, 36, 37 are intermittently bonded over full lengths thereof to the inner sheet 2 and/or the outer sheet 3 by hot melt adhesive wherein the elastic members 16, 36 extend across the front waist region 6 and the elastic members 17, 37 extend across the rear waist region 7. The front and rear waist regions 6, 7 are stretched and contracted in the transverse direction C, in other words, in the waistline direction R in FIG. 1 as these elastic members 16, 17, 36, 38 are stretched and contracted, respectively. It should be noted here that the front lateral zones 11 of the front waist region 6 are respectively formed with first front inelastic regions 51 and second front inelastic regions 52. A plurality of spot-like front joints 91 inside the second front inelastic regions 52 and these front joints 91 define the front joint areas 53. In the rear lateral zones 13 of the rear waist region 7, first rear inelastic regions 61 and second rear inelastic regions 62 are formed. Inside the second rear inelastic regions 62, a plurality of spot-like rear joints 92 are formed and these rear joints 92 define the rear joint areas 63.

The first front inelastic regions 51 include the front waist elastic members 16 extending across the front waist region 6, the front intermediate elastic members 36 extending also across the front waist region 6 and the leg elastic members 18. Of these elastic members 16, 36, 18, at least the elastic members 16, 36 may be cut at a plurality of points 55 along length thereof to form the first front inelastic regions 51. In consequence, these first front inelastic regions 51 are neither elastically stretched nor elastically contract. To cut these elastic members 16, 18, 36, cutter blades may be pressed against one of the inner sheet 2 and the outer sheet 3 from the outer side to form a plurality of cuts 56. In other word, the first front inelastic regions 51 formed in such away are areas of assembly of cuts 56. Pieces of the elastic members 16, 18, 36 created by this cutting operation remain in the first front inelastic regions 51 in each contracted state. Each of these first inelastic regions 51 is preferably dimensioned to be same as or slightly larger than a size of the front fastener member 12 attached to the first inelastic region 51. In this way, the front fastener members would not gather under contraction of the elastic members 16, 18, 36 and, in consequence, an engagement area between the front fastener members 12 and the associated rear fastener members 14 would not be substantially reduced. The second front inelastic regions 52 are formed aside inward from the associated first front inelastic regions 51 as viewed in the transverse direction C and preferably spaced from the associated first front inelastic regions 51 by a distance in a range of 5 to 15 mm. The second front inelastic regions 52 are formed by cutting at least the elastic members 16, 36 of these elastic members 16, 18, 36, respectively, each at a single point 57 in the form of cuts 58. The presence of these second front inelastic regions 52 effectively eliminate a possibility that the front fastener members 12 might be directly pulled by at least the elastic members 16, 36 of these elastic members 16, 18, 36 in the waistline direction R when the front waist region 6 and the rear waist region 7 are repetitively connected with and disconnected from each other. It should be understood here that the present invention may be exploited without forming the second front inelastic regions 52 unless such effective function of the second front inelastic regions 52 is required.

The front joints 91 may be formed by pressurizing the inner and outer sheets 2, 3 put flat together in a spot-pattern at ambient temperature or by pressurizing them in a spot-pattern under heating, or by pressurizing them together with one or more of the elastic members 16, 18, 36 in a spot-pattern at ambient temperature or under heating. As a result of such pressurizing operation, these two sheets and elastic members are integrated to film thinner than a sum of the initial thickness thereof. For example, in the case of the inner sheet 2 and/or outer sheet 3 comprising thermoplastic synthetic fibers, the thermoplastic synthetic fibers is fused together, resulting in loss of texture peculiar to the initial fiber, i.e., presents a film-like state. If both the inner sheet 2 and the outer sheet 3 are film-like sheets made of thermoplastic synthetic resin from the start, these film-like sheets are fused together to form integrated film-like sheet which is thinner than a summed thickness of the inner sheet 2 and the outer sheet 3. Preferably, the inner sheet 2 and/or the outer sheet 3 may be pressurized under heating to form the front joints 91 wherein at least one of these sheets 2, 3 is melt-solidified. These front joints 91 are formed immediately inside the respective second front inelastic regions 52 as viewed in the waistline direction R in FIGS. 1 and 2 so as to extend in the vertical direction B from the waist-opening 31 to the leg-openings 31 over a range substantially same as or longer than the first front inelastic regions 51 (See FIGS. 1 and 2). The expression "the front joints 91 in a spot-pattern" means that a plurality of joints 91 are intermittently distributed at least in the vertical direction A. While any particular shape of the individual front joints 91 is not specified, each of them is preferably circular dot having a diameter in a range of 0.5 to 5 mm.

With the diaper 1 having the front joint areas 53 comprising such front joints 91, should the inner sheet 2 and/or the outer sheet 3 be broken or torn in the vicinity of the front fastener members 12 in the course of handling the front fastener members 12, the front joints 91 reliably prevent such break or tear from being further propagated. For example, even when there is concern that the component fibers of nonwoven fabric might be forcibly drawn apart one from another and, in consequence, a local break of nonwoven fabric might propagate, the front joints 91 reliably prevent the component fibers from being drawn apart because the front joints 91 respectively comprise a plurality of component fibers integrated in a film-like state to prevent propagation of the break or tear. Assumed that the second front inelastic regions 52 are not provided, the front joints 91 will be preferably spaced from the associated first inelastic regions 51 by a distance of 5 to 30 mm.

The first rear inelastic regions 61 are formed by cutting the rear waist elastic members 17, the leg elastic members 18 and the rear intermediate elastic members 37 included therein, more specifically at least the elastic members 17, 37 thereof, at a plurality of points 65 along length thereof. In consequence, these first rear inelastic regions 51 can be neither elastically stretched nor elastically contracted in the transverse direction C. These elastic members 17, 18, 37 may be cut by the cutter blade to form cuts 66 which are similar to the cuts 56 in the case of the elastic members 16, 18, 36. Each of these first rear inelastic regions 61 is preferably dimensioned to be same as or slightly larger than a size of the rear fastener member 14 attached to the first inelastic region 61. In this way, the rear fastener members 14 would not be formed with gathers undulating in the transverse direction C, i.e., in the waistline direction R in FIG. 1. The second rear inelastic regions 62 are formed aside inward from the associated first rear inelastic regions 61 as viewed in the transverse direction C and preferably spaced from the associated first rear inelastic regions 61 by a distance in a range of 5 to 15 mm. The second rear inelastic regions 62 are formed by cutting at least the elastic members 17, 37 of these elastic members 17, 18, 37 to define cuts 68 each at least a single point 67. The presence of these second rear inelastic regions 62 prevent the rear fastener members 14 from being directly pulled by the elastic members 17, 18, 37 in the waistline direction R when the front waist region 6 and the rear waist region 7 are repetitively connected with and disconnected from each other. It should be understood here that the present invention may be implemented without forming the second rear inelastic regions 62 unless such effective function of the second rear inelastic regions 62 is required.

Figure 4:
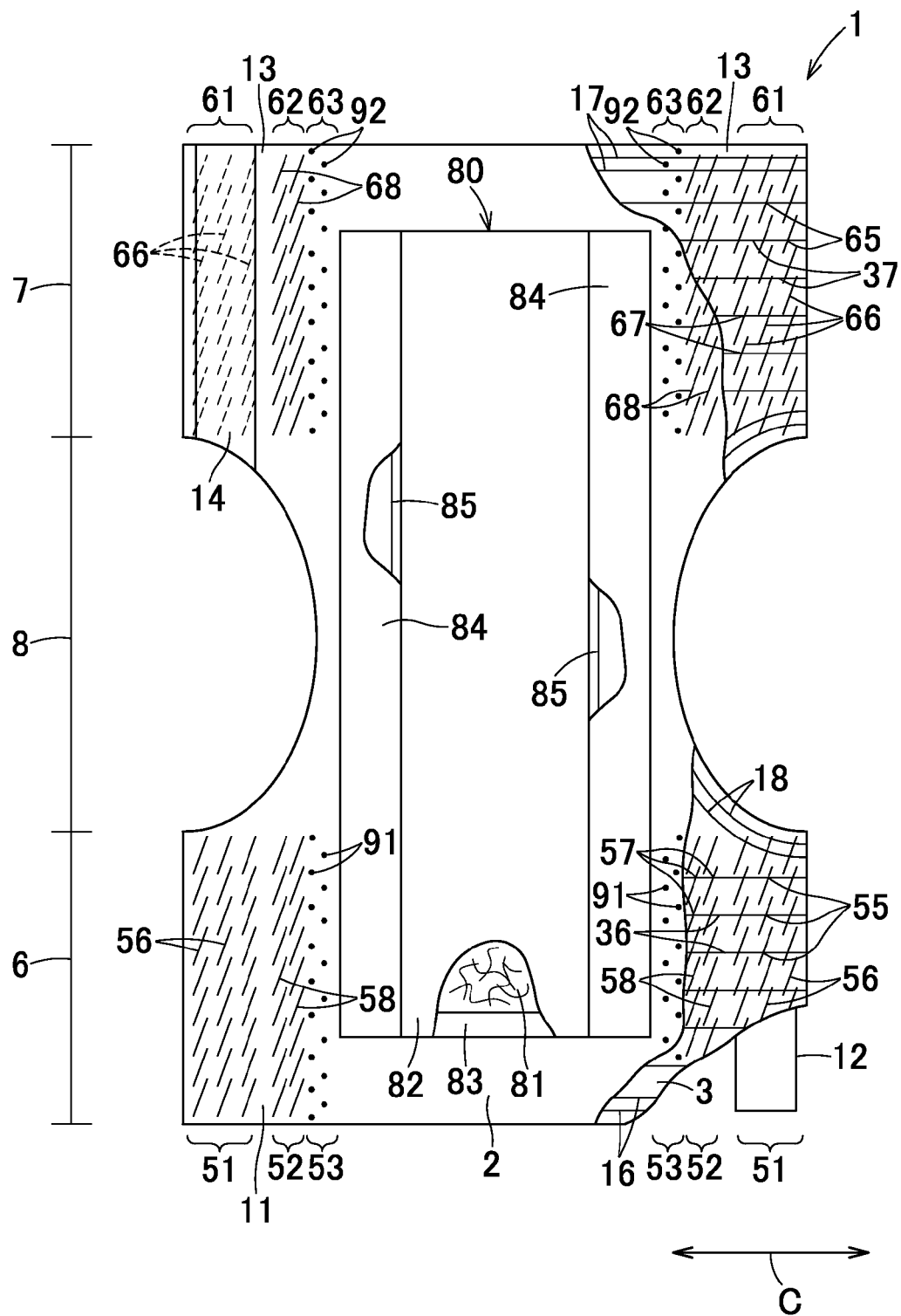
FIG. 4 is a view similar to FIG. 3, showing one preferred embodiment of the invention.

According to the embodiment shown by FIG. 4, the rear joints 92 are formed in the similar manner as the front joints 91 except that these rear joints 92 formed immediately inside the second rear inelastic regions 62. These rear joints 92 are similar to the front joints 91 with respect to the shape as well as the size and intermittently distributed over the all range defined between the waist-opening 31 and the leg-openings 32. With the diaper 1 having the rear joint areas 63 comprising such rear joints 92, should the inner sheet 2 and/or the outer sheet 3 be broken or torn in the vicinity of the rear fastener members 14 in the course of handling the rear fastener members 14, the rear joints 91 reliably prevent such break or tear from being further propagated. Assumed that the second rear inelastic regions 62 are not provided, the rear joints 92 will be preferably spaced apart from the associated first rear inelastic regions 61 by a distance of 5 to 30 mm.

While each of the front fastener members 12 is divided into upper and lower halves according to the particular embodiment of the invention shown by FIG. 1 so that the front lateral zones 11 are easily deformed between the upper and lower halves of the respective front fastener members 12 and thereby improve fitness to the wearer's body. However, the front fastener members 12 each divided into the upper and lower halves may be replaced by the not divided but continuous front fastener members 12 unless such effect is required.

While the rear fastener members 14 is implemented in the form of the loop members adapted to be engaged with the associated front fastener members 12 in the illustrated embodiment, the inner sheet 2 to which these rear fastener members 14 are attached may replace the rear fastener members 14 so far as the inner sheet 2 can be repetitively engaged with and disengaged from the associated front fastener members. Regarding the fasteners 20 in the illustrated embodiment, it is possible to use the loop members of the mechanical fastener as the front fastener members 12 and to use the hook members adapted to be engaged with the associated loop members as the rear fastener members 14. Furthermore, it is also possible to attach the front fastener members 12 to the inner surface of the front lateral zones 11 and to attach the rear fastener member 14 to the inner surface of the rear lateral zones 13.

FIG. 4 is a view similar to FIG. 3, showing one preferred embodiment. In the diaper 1 shown in FIG. 4 as has been flatly developed, the core 4 in FIG. 3 is replaced by a body fluid absorbent panel 80 attached to the inner surface of the inner sheet 2. The panel 80 comprises a body fluid absorbent core 81, a liquid-pervious sheet 82 covering the upper surface of the core 81 and a liquid-impervious thermoplastic synthetic resin film sandwiched between the core 81 and the inner sheet 2. The panel 80 is provided along transversely opposite side edges thereof with leak-barriers themselves known art, respectively. With the diaper 1 put on the wearer's body these leak-barriers 84 raise themselves from the panel 80 toward the wearer's skin so that these leak-barriers 84 would be held in contact with the wearer's thighs with fitness required to prevent body fluids from leaking sideways. Each of the leak-barriers 84 includes an elastic member 85 extending under tension in the longitudinal direction of the leak-barrier 84. In this diaper 1, the inner sheet 2 and the outer sheet 3 are bonded to each other by adhesive (not shown) coated on these sheets 2, 3 so as to be uniformly distributed thereon. According to this embodiment also, the elastic members 16, 17, 18, 36, 37 are attached under tension so as be sandwiched between these sheets 2, 3 and, similarly to the embodiment shown in FIG. 3, the front lateral zones 11 and the rear lateral zones 13 are formed with the first and second front inelastic regions 51, 52 and the first and second rear inelastic regions 61, 62, respectively. In the embodiment shown by FIG. 4, the front lateral zones 11 and the rear lateral zones 13 are further provided with the front joint areas 53 defined by the front joints 91 and the rear joint areas 63 defined by the rear joints 92, respectively. The front fastener members 12 are attached to the first front inelastic regions 51 and the rear fastener members 14 are attached to the first rear inelastic regions 61. To make such diaper 1, a composite sheet consisting of the inner and outer sheets 2, 3 put flat and bonded together may be previously prepared and then the panel 80 may be attached to such composite sheet by adhesive. The embodiment shown in FIG. 4 is distinguished from the embodiment shown in FIG. 3 in that it is possible to use a liquid-impervious thermoplastic synthetic resin film may be used as the inner sheet 2.

FIG. 5 is a schematic diagram partially illustrating a production process for the diaper 1 shown by FIG. 1 wherein a machine direction is indicated by an arrow MD and a direction orthogonal to the machine direction MD is indicated by a double-headed arrow CD.

Referring to FIG. 5, in a step I, respective continuous materials 116, 117, 118, 136 and 137 for the front waist elastic members 16, the rear waist elastic members 17, the leg elastic members 18, the front intermediate elastic members 36 and the rear intermediate elastic members 37 are attached to a web 103 which is continuous material for the outer sheet 3 being fed in the machine direction MD by hot melt adhesive (not shown). The continuous material 118 for the leg elastic members 18 comprises continuous material 118a and continuous material 118b describing sine curves intersecting with each other.

In a step II, the panel-like body fluid absorbent cores 4 are at intervals attached to the web 103 at predetermined locations thereon as viewed in the machine direction MD by hot melt adhesive (not shown).

In a step III, web 102 which is continuous material for the inner sheet 2 is fed in the machine direction MD so as to cooperate with the web 103 to sandwich the continuous materials 116, 117, 118, 136, 137 of the respective elastic members and the individual cores 4. Specifically, the web 103 and the web 102 are put flat and bonded together by hot melt adhesive (not shown) intermittently and uniformly coated on one of these two webs 102, 103 to form first composite web 171. This first composite web 171 is elastically stretchable and contractible in the machine direction MD.

In a step IV, the first composite web 171 is fed into a roll nip defined between a first roll 161 and a second roll 162 adapted to rotate at a predetermined velocity and to cooperate together to form a cutter 160 so as to cut the continuous materials 116, 117, 118, 136 and 137 for the respective elastic members locally in a region defined between each pair of the adjacent cores 4, 4 and to form a plurality of cuts 55, 57, 65 and 67. In this way, the step IV results in formation of a second composite web 172 having a plurality of cuts 55, 57, 65, 67 as seen in FIG. 3, the first and second front inelastic regions 51, 52 cyclically arranged in the machine direction MD and the first and second rear inelastic regions 61, 62 cyclically arranged in the machine direction MD in a manner similar to the first and second front inelastic regions 51, 52. The step IV further includes a sub-step of using the first and second rolls 161, 162 to form the front joint areas 53 comprising the front joints 91 and the rear joint areas 63 comprising the rear joints 92 as shown in FIGS. 1 through 3.

In a step V, the front fastener members 12 shown in FIG. 1 are attached to the web 102 constituting the second composite web 172 in the first front inelastic regions 51 while the rear fastener members 14 are attached to the web 103 constituting the second composite web 172 in the first rear inelastic regions 61. The step V further includes a sub-step of cutting out disc-like laminate 184 consisting of the webs 102, 103 put flat and bonded together from the second composite web 172 between each pair of the adjacent cores 4 to obtain a third composite web 173 formed with openings 132.

In a step VI, the third composite web 173 is cut along respective center lines T (See the steps IV and V) extending in the cross direction CD between each pair of the adjacent cores 4, 4 and the rear fastener members 14 are engaged with the associated front fastener members 12 to obtain the individual pants-like diapers 1. By cutting the third composite web 173 in this manner, the first and second front inelastic regions 51, 52, the first and second rear inelastic regions 61, 62, the front joint areas 53 and the rear joint areas 63 are obtained on both sides of the respective center lines T. At the same time, the openings 132 are respectively bisected so as to form the respective peripheral edges of the leg-openings 32.

FIG. 6 illustrates a portion of the first roll 161 constituting the cutter 160 used in the production process illustrated in FIG. 5 as has been flatly developed. The first roll 161 is used with a second roll 162 having a smooth peripheral surface (not shown) wherein some (117, 137) of the elastic members to be cut by the cutter 160 are indicated by imaginary lines. The first roll 161 is formed on the peripheral surface 164 thereof with a plurality of blade segments 180 and a plurality of pins 190 in the form of columnar projections.

These blade segments 180 radially project from the peripheral surface 164 and serve to cut the respective continuous materials 116, 117, 118, 136 and 137 lying between these blade segments 180 and a peripheral surface of the second roll 162 under a pressure with or without heating. Such blade segments 180 are arranged intermittently in an axial direction X to form a blade array 181. The first roll 161 has a plurality of the blade arrays 181 extending in parallel one to another and, in FIG. 6, first through fifth pairs of blade arrays 181a through 181e are arranged so as to be symmetric one with another about an imaginary line S extending in the axial direction X. On the first roll 161, the first, second and third blade arrays 181a, 181b, 181c are used to form the diaper 1 with the first front inelastic regions 51 and the first rear inelastic regions 61. The fourth and fifth blade arrays 181d, 181e are used to form the diaper 1 with the second front inelastic regions 52 and the second rear inelastic regions 62. According to a preferred first roll 161, the angle at which the individual blade segments 180 are oblique with respect to the axial direction X as well as the distance in the axial direction X by which each pair of the adjacent blade segments 180 are spaced from each other are substantially common to all of the blade arrays 181. In each of the blade arrays 181, the individual blade segments 180 are arranged in a unique manner. More specifically, assumed that these individual blade segments 180 are moved in a circumferential direction, each pair of the blade segments 180 adjacent in the axial direction X will partially overlap each other and provide a same effect as a single blade continuously extending in the axial direction X will provide. Consequentially, the respective continuous materials 116, 117, 118, 136 and 137 for the respective elastic members extending in the machine direction MD as shown by FIG. 5 are reliably cut by these blade arrays 181.

The pins 190 are used to pressurize the first composite web 171 sandwiched between these pins 190 and the second roll 162 with or without heating and thereby to form the front joints 91 and the rear joints 92.

The blade segments 180 and the pins 190 may be heated at a desired temperature to facilitate the continuous materials 116, 117, 118, 136 and 137 for the respective elastic members to be cut, to melt-solidify regions of nonwoven fabric or film-like sheet forming the web 102 and the web 103 being in contact with the blade segments 180, and to assist the pins 190 to form the front joints 91 and the rear joints 92. The second roll 162 also is adapted to be adjustably heated at a desired temperature. A distance by which the first roll 161 and the second roll 162 are spaced from each other is adjustable. Even under such conditions, the web 102 and/or the web 103 might be damaged when the continuous materials 116, 117, 118, 136, 137 for the respective elastic members are cut by the blade segments 180. In such a case, the component fibers forming the nonwoven fabric might be drawn apart and/or break or tear of the film-like sheet might propagate in the course of the cutting operation. However, the regions of the nonwoven fabric or the film-like sheet being in contact with the blade segments 180 and/or the pins 190 may be melt-solidified to prevent such damage from propagating.

With the cutter 160 comprising the roll pair, a clearance (not shown) between the blade segments 180 and the second roll 162 is set to be smaller than a clearance between the pins 190 and the second roll 162. The first composite web 171 fed in the machine direction MD so as to be guided through the roll nip defined between the first roll 161 and the second roll 162 is pressurized by the pins 190 cooperating with the second roll 162 and then by the blade segments 180 cooperating with the second roll 162. Such unique process of pressurization in incremental steps is effective to reduce the risk that the first composite web 171 might be damaged in comparison with the case in which the first composite web 171 is pressurized at one stroke.

The method exemplarily illustrated in FIG. 5 as well as the roll 161 exemplarily shown in FIG. 6 should not be construed to impose limitations to the present invention and may be appropriately varied or modified depending on the particular shape and construction of the diaper 1. For example, it is possible to design the step V so that the third composite web 173 may be folded back onto itself along a center line W (See FIG. 5) bisecting a transverse dimension of this composite web 173 to obtain the diaper 1 which has been flatly folded back on itself having the front fastener members 12 and the rear fastener members 14 put in engagement. The number of the blade arrays 181 as well as the circumferential distance between each pair of the adjacent blade arrays 181 on the first roll 161 may be appropriately selected. Furthermore, the length of the individual blade segments 180, the inclination angle of the individual blade segments 180 with respect to the axial direction X and the distance between each pair of the adjacent blade segments 180 in the respective blade arrays 181 may be also appropriately selected. Concerning the pins 190 also, it is possible to vary the tip's shape, the tip's diameter and the distribution pattern of these pins on the first roll 161. For the method according to the present invention, the order in which the first composite web 171 is formed with the first and second front inelastic regions 51, 52, the first and second rear inelastic regions 61, 62, the front joint areas 53 and the rear joint areas 63 is not specified. For example, it is possible to form the first composite web 171 with the front melt-solidified joints 91 and the rear melt-solidified regions 92 using a roll pair provided separately of the first and second rolls 161, 162 after the first composite web 171 has been formed with the first and second front inelastic regions 51, 52 as well as the first and second rear inelastic regions 61, 62 using the first and second rolls 161, 162. It is also possible to form the first composite web 171 with the second front inelastic regions 52 and the second rear inelastic regions 62 using a roll pair provided separately of the first and second rolls 161, 162 after the first composite web 171 has been formed with the first front inelastic regions 51 and the first rear inelastic regions 61 using the first and second rolls 161, 162.

The present invention as has been described on the basis of the disposable diaper as the typical example may be exploited also, for example, in the form of a toilet-training pant, incontinent briefs or a disposable pant.

The invention claimed is:

1. A pant-type wearing article comprising:
   a first waist region defined by one of front and rear waist regions;
   a second waist region defined by the other of said front and rear waist regions;
   a crotch region extending between said first and second waist regions;
   second fastener members provided along transversely opposite lateral zones of said second waist region and having inner surfaces;
   first fastener members provided along transversely opposite lateral zones of said first waist region and having outer surfaces so that the inner surfaces of said second fasteners are detachably engaged with the outer surfaces of said first fastener members to produce a pant-type wearing article having a waist-opening and a pair of leg-openings formed upon engagement;

at least one of said first waist region and said second waist region includes a plurality of elastic members bonded thereto under tension so as to extend across said one waist region and, in said transversely opposite lateral zones of said one of waist regions, said elastic members are respectively cut at several points in a longitudinal direction thereof to form first inelastic regions being neither elastically stretchable nor elastically contractible in said longitudinal direction;

either said first fastener members or said second fastener members both provided in said one of waist regions are provided in said first inelastic regions;

in said transversely opposite lateral zones of said one of waist regions, inside the first inelastic regions and inside one of the fastener members as viewed in a waistline direction, said elastic members are respectively cut at several points in a longitudinal direction thereof to form second inelastic regions being neither elastically stretchable nor elastically contractible in said longitudinal direction;

between each of the first inelastic regions and the second inelastic regions, a region in which none of the elastic members is cut is formed inside the one of the fastener members;

transversely opposite lateral zones of said one of waist regions are formed inside said second inelastic regions as viewed in a waistline direction with a plurality of film-like joints comprising sheet members put flat together to define said transversely opposite lateral zones and integrated or comprising said sheet members and said elastic members integrated and said joints define joint areas extending in a vertical direction of said wearing article from said waist-opening to said leg-openings.

2. The wearing article as defined by claim 1, wherein at least one of said sheet members put flat together comprises thermoplastic synthetic fibers and, at a plurality of said points at which said elastic members are cut, components of said thermoplastic synthetic fibers are melt-solidified together.

3. The wearing article as defined by claim 1, wherein said sheet members are melt-solidified together at said joints.

4. The wearing article as defined by claim 1, wherein
said first fastener members are formed of hook members and respectively divided into upper and lower portions spaced apart from each other in said vertical direction;
said second fastener members are formed of loop members and respectively extend continuously in said vertical direction.

5. The wearing article as defined by claim 4, wherein at least one of said sheet members put flat together comprises thermoplastic synthetic fibers and, at a plurality of said points at which said elastic members are cut, components of said thermoplastic synthetic fibers are melt-solidified together.

6. The wearing article as defined by claim 4, wherein said sheet members are melt-solidified together at said joints.

7. The wearing article as defined by claim 4, wherein
said first inelastic region is formed at least in said first waist region;
said elastic members are respectively cut in regions where said upper portions of said first fastener members are formed, in regions where said lower portions of said first fastener members are formed, and in regions between said upper and lower portions of said first fastener members.

8. The wearing article as defined by claim 7, wherein said sheet members are melt-solidified together at said joints.

9. The wearing article as defined by claim 7, wherein at least one of said sheet members put flat together comprises thermoplastic synthetic fibers and, at a plurality of said points at which said elastic members are cut, components of said thermoplastic synthetic fibers are melt-solidified together.

10. The wearing article as defined by claim 1, wherein cutting lines which cut said elastic members in said first inelastic regions are oblique as viewed in said vertical direction.

11. The wearing article as defined by claim 10, wherein said sheet members are melt-solidified together at said joints.

12. The wearing article as defined by claim 10, wherein at least one of said sheet members put flat together comprises thermoplastic synthetic fibers and, at a plurality of said points at which said elastic members are cut, components of said thermoplastic synthetic fibers are melt-solidified together.

13. A method for making a pant-type wearing article comprising:
a first waist region defined by one of front and rear waist regions;
a second waist region defined by other of said front and rear waist regions;
a crotch region extending between said first and second waist regions;
wherein respective inner surfaces of second fastener members provided along transversely opposite lateral zones of said second waist region are detachably engaged with respective outer surfaces of said first fastener members provided along transversely opposite lateral zones of said first waist region to produce a pant-type wearing article having a waist-opening and a pair of leg-openings formed upon engagement, said method comprising:
providing at least one waist region of said first waist region and said second waist region with a plurality of elastic members bonded thereto under tension so as to extend across said one waist region and, in said transversely opposite lateral zones of said one waist region:
cutting said elastic members respectively at several points in a longitudinal direction thereof to form first inelastic regions being neither elastically stretchable nor elastically contractible in said longitudinal direction;
providing either said first fastener members or said second fastener members in said said first or second waist regions in said first inelastic regions;
in said transversely opposite lateral zones of said one of waist regions, inside the first inelastic regions and inside one of the fastener members as viewed in a waistline direction, said elastic members are respectively cut at several points in a longitudinal direction thereof to form second inelastic regions being neither elastically stretchable nor elastically contractible in said longitudinal direction;
between each of the first inelastic regions and the second inelastic regions, a region in which none of the elastic members is cut is formed inside the one of the fastener members;
forming transversely opposite lateral zones of said one waist region inside said inelastic regions as viewed in a waistline direction with a plurality of film-like joints comprising sheet members put flat together to define said transversely opposite lateral zones and integrated or comprising said sheet members and said elastic members integrated and said joints define joint areas extending in a vertical direction of said wearing article from said waist-opening to said leg-openings; and
said first and second inelastic regions and said joint areas are formed by following at least the steps of:

a) subjecting a composite web to a cutter at regular intervals in machine direction, wherein said composite web comprises first and second webs put flat and bonded together by adhesive and continuously fed in said machine direction and a plurality of continuous elastic members sandwiched between said first and second webs so as to extend in said machine direction and bonded under tension to at least one of said first and second webs, and thereby cutting said continuous elastic members at several points within predetermined ranges of said composite web to obtain said first and second inelastic regions within said predetermined ranges; and b) using a plurality of pins, with or without heating, to pressurize, said composite web in a plurality of points lying inside said predetermined ranges of said composite web to be formed with said second inelastic regions as viewed in said machine direction, wherein the composite web comprises said first and second webs put flat and bonded together by adhesive and continuously fed in said machine direction and a plurality of said continuous elastic members sandwiched between said first and second webs so as to extend in said machine direction and bonded under tension to at least one of said first and second webs in a plurality of points lying inside said predetermined ranges of said composite web to be formed with said inelastic regions as viewed in said machine direction and thereby forming a plurality of joints at which said first web and said second web are integrated together in a film or at which said first web, said second web and said continuous elastic members are integrated together in a film so that these joints are distributed in a cross direction with respect to said machine direction and thereby said joint areas are obtained.

14. The method as defined by claim 13, wherein at least one of said first and second webs comprises thermoplastic synthetic fiber and said cutter and said pins constituting a single roll adapted to be rotated in said machine direction and to be heated so that components of said thermoplastic synthetic resin are melt-solidified together at a plurality of said points at which said continuous elastic members are cut and a plurality of said points at which said joints are formed.

* * * * *